United States Patent [19]

Asato

[11] 4,051,183

[45] Sept. 27, 1977

[54] 1-BENZOYL-3-(1,2,3,4-TETRAHYDRO-4-OXO-1-NAPHTHYL)-UREA, A NOVEL AND USEFUL INTERMEDIATE FOR THE PREPARATION OF ANIMAL GROWTH PROMOTING AGENTS

[75] Inventor: Goro Asato, Titusville, N.J.

[73] Assignee: American Cyanamid Company, Stamford, Conn.

[21] Appl. No.: 720,164

[22] Filed: Sept. 2, 1976

[51] Int. Cl.$^2$ ................ C07C 127/19; C07C 127/22; A61K 31/17

[52] U.S. Cl. .................. 260/553 A; 260/453 AR; 260/553 E; 260/562 R; 260/578; 424/322

[58] Field of Search ................ 260/553 A, 553 E

[56] References Cited

U.S. PATENT DOCUMENTS

| | | | |
|---|---|---|---|
| 2,870,159 | 1/1959 | Bloom | 260/553 A X |
| 2,870,160 | 1/1959 | Bloom | 260/553 A X |
| 2,870,161 | 1/1959 | Bloom | 260/553 A X |
| 3,542,850 | 11/1970 | Jansen et al. | 260/562 N X |
| 3,903,077 | 9/1975 | Jones et al. | 260/562 N X |
| 3,953,506 | 4/1976 | Spicer et al. | 260/553 A |
| 3,993,677 | 11/1976 | Asato | 260/553 A X |

*Primary Examiner*—Daniel E. Wyman
*Assistant Examiner*—Thomas A. Waltz
*Attorney, Agent, or Firm*—Edward A. Conroy, Jr.

[57] ABSTRACT

This invention relates to 1-benzoyl (and 1-substituted benzoyl)-3-(1,2,3,4-tetrahydro-4-oxo-1-naphthyl)ureas, novel and useful intermediates for the preparation of 1,2,3,4-tetrahydro-4-oxo-1-naphthylurea and certain derivatives thereof. The above tetrahydro-4-oxo-1-naphthyl-urea and certain derivatives thereof are animal growth promoting agents.

This invention further relates to methods of preparation of said 1-benzoyl (and 1-substituted benzoyl) 3-(1,2,3,4-tetrahydro-4-oxo-1-naphthyl)ureas.

6 Claims, No Drawings

1-BENZOYL-3-(1,2,3,4-TETRAHYDRO-4-OXO-1-NAPHTHYL)-UREA, A NOVEL AND USEFUL INTERMEDIATE FOR THE PREPARATION OF ANIMAL GROWTH PROMOTING AGENTS

BACKGROUND OF THE INVENTION

The 1-benzoyl (and 1-substituted benzoyl)-3-(1,2,3,4-tetrahydro-4-oxo-1-naphthyl)ureas are useful and valuable intermediates for the preparation of 1,2,3,4-tetrahydro-4-oxo- 1-naphthylurea (and certain derivatives thereof) which possesses animal regulating activity; said tetrahydro- 4-oxo-1-naphthylurea (and certain derivatives thereof) having been described and claimed in the application for U.S. letters patent Ser. No. 582,559, filed May 30, 1975 (Goro Asato, inventor), now abandoned, which is herein incorporated by reference.

SUMMARY OF THE INVENTION

This invention relates to novel compounds of formula (I):

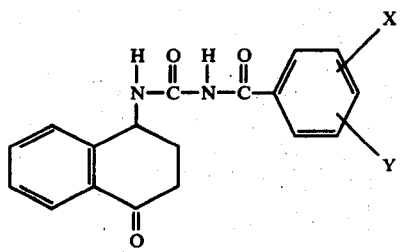

(I)

wherein X is selected from the group consisting of hydrogen, methyl, methoxy, chloro, and nitro; and Y is selected from the group consisting of hydrogen, chloro and nitro.

This invention also relates to the racemic mixtures and to the optically active forms of the ureas identified hereinabove by formula (I). The optionally active forms are designated as the (1R) and the (1S) isomers with the (1S) isomer generally being preferred since 1,2,3,4-tetrahydro-4- oxo-1-naphthylurea (and certain of its derivatives) derived therefrom appears to be biologically more active than the (1R) isomer. The preferred (1S) isomer can be illustrated as follows:

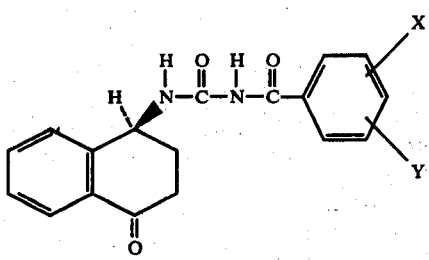

(II)

the corresponding (1R) isomer can be illustrated as follows:

(III)

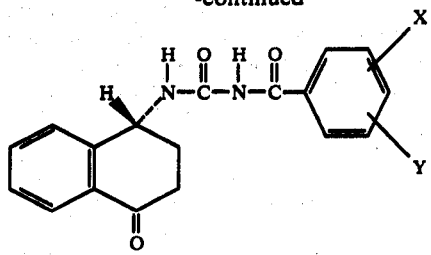

Hereinafter the terms (R) and (S) will refer to the absolute configuration at the 1-position.

The above-identified formulae II and III optically active urea compounds have the same absolute configuration at the 1-position of the 1,2,3,4-tetrahydro- 4-oxo-naphthylene as the 1,2,3,4-tetrahydro-1-naphthylamine used as starting material. In order to obtain the formula II (S) isomer or the formula III (R) isomer, it is necessary to start with the corresponding (S) and (R) isomer of 1,2,3,4-tetrahydro-1- naphthylamine or an appropriate derivative thereof.

The resolved 1,2,3,4-tetrahydro-1-naphthylamines have been reported in the literature by R. Weidmann and J. P. Guette, Comptes Rendus des Seances de l'Academie des Sciences 268: 2225 (1969), as resulting from the Curtius reactions with the optically active 1,2,3,4-tetrahydro- naphthalenecarboxylic acid azides. This work establishes the absolute configuration of the (R) and (S) isomers, but does not suggest the 1-benzoyl-3-(1,2,3,4-tetrahydro-4-oxo-1- naphthyl)urea of the present invention, nor does it provide a practical preparative method for obtaining the isomers in a high state of purity.

This invention also relates to methods for the preparation of the above-identified formula (I) ureas.

In accordance with this invention, the novel formula (I) 1-benzoyl-3-(1,2,3,4-tetrahydro-4-oxo-1-naphthyl)-ureas, wherein said ureas may be the racemic mixtures, or the optically active isomers thereof, can be conveniently prepared, as hereinbelow described and illustrated in detail.

The precursor, formula (V) 1,2,3,4-tetrahydro-4-oxo-1-naphthylamine, can be prepared by the route illustrated below:

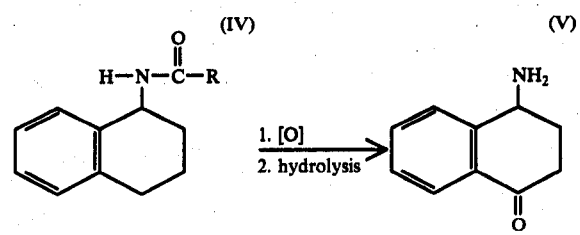

wherein R is hydrogen or alkyl $C_1$-$C_4$.

One equivalent of a formula (IV) amide is reacted with 2 to 8 eqivalents, preferably with 2 to 5 equivalents, of an oxidizing agent selected from the group consisting of ceric ammonium nitrate, ceric sulfate, chromic anhydride, sodium or potassium bichromate and the like, at a temperature from about 0° C to about 100° C, preferably 20° to 60° C, in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or the oxidizing agent chromic anhydride in acetic anhydride, followed by hydrolysis to yield the formula (V) 1,2,3,4-tetrahydro-4-oxo-1-naphthylamine, or an acid addition salt thereof when the hydrolyzing agent selected in an acid (e.g., hydrochloric acid).

While all oxidation reactions may not be effective, nevertheless, the oxidation of a formula (IV) amide to the corresponding formula (V) oxoamine is novel and undisclosed.

A compound of formula (I) can be prepared by reacting the formula (V) amine (or an acid addition salt thereof) with benzoyl (or a substituted benzoyl) isocyanate as graphically illustrated below:

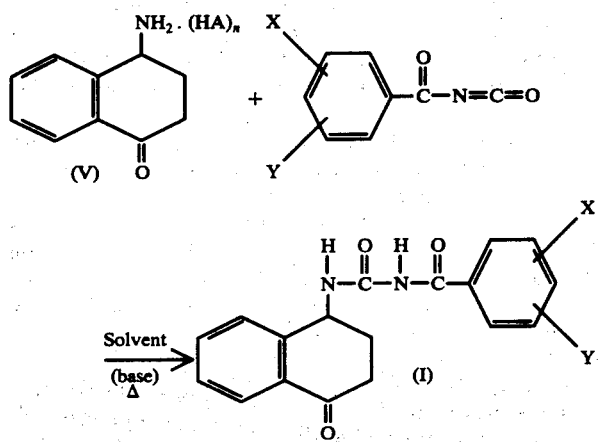

wherein X is selected from the group consisting of hydrogen, methyl, methoxy, chloro and nitro; Y is selected from the group consisting of hydrogen, chloro and nitro; and HA represents an acid such as hydrochloric, hydrobromic and hydriodic acid, wherein $n$ is 0 or 1.

The reaction can be carried out using approximately equimolar amounts of the isocyanate and the amine, or the acid addition salt thereof; however, it is generally preferable to employ from about 5% to about 50% excess of the isocyanate. The reaction can be conducted at atmospheric or superatmospheric pressure and at a temperature in the range of from about 0° to about 100° C, but is preferably conducted at atmospheric pressure at from about 0° to about 70° C, in the presence of an organic solvent.

Suitable organic solvents include aprotic aromatic solvents such as benzene, toluene and xylene; chlorinated hydrocarbon solvents such as methylene chloride, chloroform and dichloroethane; ethers such as tetrahydrofuran, diethyl ether, dimethoxyethane; lower alkyl $C_1$–$C_4$ ketones such as acetone, methyl ethyl ketone, methyl butyl ketone and methyl isobutyl ketone, or mixtures of said solvents.

When the above reaction is carried out using a formula V amine acid addition salt, it is desirable to add an acid acceptor to the reaction mixture. Suitable acid acceptors include trialkylamines such as triethylamine, trimethylamine, pyridine or the like, alkali metal carbonates such as sodium or potassium carbonate; alkaline earth carbonates such as calcium carbonate; strong basic ion exchange resins, and aqueous alkali in a 2-phase system using an immiscible hydrocarbon solvent such as benzene, toluene, or a chlorinated hydrocarbon such as chloroform or dichloroethane.

Alternatively, 1,2,3,4-tetrahydro-1-naphthylamine of formula (VI) can be reacted with benzoyl (or substituted benzoyl) isocyanate by the procedure hereinabove described, to yield a 1-benzoyl-3-(1,2,3,4-tetrahydro-1-naphthyl)urea of formula (VII). This reaction can be graphically illustrated as follows:

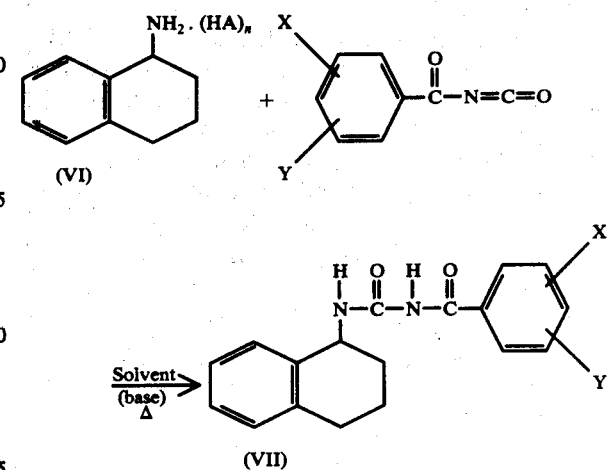

wherein X, Y, HA and $n$ are as previously defined.

The benzoylurea of formula (VII), with the proviso that X and Y cannot be methyl, is then oxidized by a procedure analogous to the one utilized in the preparation of 1,2,3,4-tetrahydro-4-oxo-1-naphthylamine of formula (V), as hereinabove described in detail, to yield the novel 1-benzoyl-3-(1,2,3,4-tetrahydro-4-oxo-1-naphthyl)ureas of formula (I) of the present invention, as illustrated below:

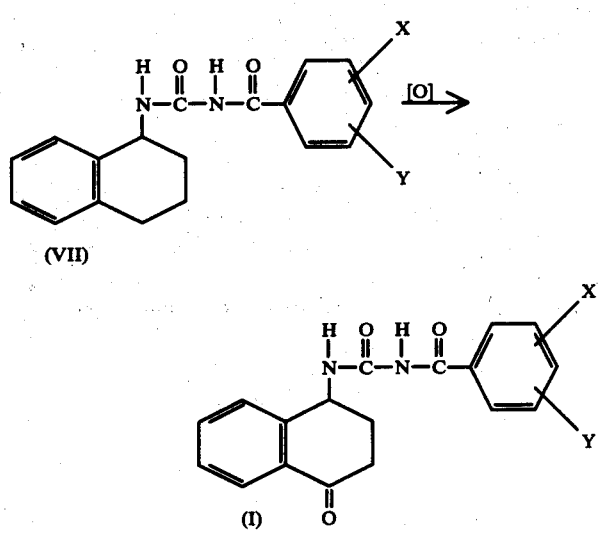

While all oxidation reactions may not be effective, nevertheless, the oxidation of formula (VII) 1-benzoyl-3- (1,2,3,4-tetrahydro-1-naphthyl)ureas to the corresponding formula (I) oxo derivatives is novel and undisclosed. Other blocking groups that are removable to hydrolysis may be used instead of the benzoyl group, and while some may give higher yields and/or easier workup, the net effect is the same in all cases, that is to protect the urea function during the oxidation step (for the conversion of formula (VII) type of urea to the correspoding formula (I) type of oxo-urea).

Acid or alkaline hydrolysis of the novel compounds of formula (I) yields 1,2,3,4-tetrahydro-4-oxo-1-naphthylurea of formula (VIII), a valuable animal growth promoter; as graphically illustrated below:

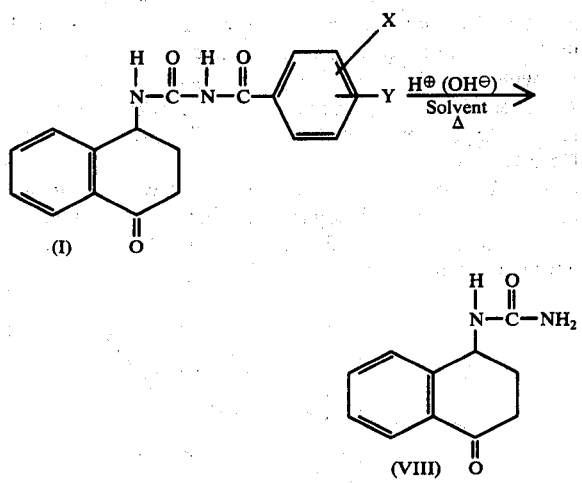

Thus, 1 equivalent of a compound of formula (I) is mixed with 1 to 10 equivalents of an aqueous acid such as hydrochloric, hydrobromic, hydriodic acid and the like, or with an aqueous base such as sodium or potassium hydroxide and the like, and, if desired, a water-miscible solvent such as $C_1$-$C_3$ alcohols, lower aliphatic ketones, dioxane, tetrahydrofuran and the like may be added to the above-said mixture. The reaction mixture is then stirred and heated at a temperature range from about 20° to about 100° C, preferably 40° to 80° C, for a period of time from about 1 hour to about 8 hours, or until the hydrolysis of said formula (I) compound is complete.

The compounds of formulae (I) and (VIII) obtained by the above procedures are the racemic mixtures.

Should the optically active forms of the novel 1-benzoyl-3-(1,2,3,4-tetrahydro-4-oxo-1-naphthyl)ureas of formula (I) be desired, or the urea of formula (VIII) derived therefrom, it is necessary to start with the corresponding optically active (S) or (R) isomer of 1,2,3,4-tetrahydro- 1-naphthylamine or an appropriate derivative thereof.

A preparation is described hereinbelow whereby the desired optical isomers of the above-said amine or certain derivatives thereof can be obtained in high yields.

The racemic mixture is treated with the appropriate (optically active) N-benzoyl glutamic acid. The (S)-(+)- 1,2,3,4-tetrahydro-1-naphthylamine forms a water insoluble salt with (+) -N-benzoyl-(R)-glutamic acid which can be crystallized out in high yield while the corresponding (R)- amine salt stays in solution. It is not necessary to employ more than about 1 mole of the resolving acid for each two moles of racemic amine, as a cheaper acid, preferably acetic, can be substituted for the balance of required acid. In this way it is possible to obtain a high yield of the desired (S)- (+) -amine based on the resolving acid. The resolved salt, (S)-(+)-1,2,3,4-tetrahydro-1-naphthylamine. i.e. raise (+)- N-benzoyl-(R)-glutamic acid salt, is treated with alkali which liberates the (S)-(+)-amine, which separates as an insoluble phase. It can be mechanically separated from the aqueous phase or extracted with a suitable solvent.

As stated above, 1,2,3,4-tetrahydro-4-oxo-1-naphthylurea is a useful animal growth promoting agent for farm animals such as cattle, sheep, horses and swine, for fur-bearing animals such as foxes, rabbits, chinchillas and the like and for companion animals such as dogs and cats.

It can be administered to said animals in their diet, generally from about 0.0001 to about 0.08% by weight, preferably from about 0.001% to about 0.04% by weight of feed. Said formula (VIII) compound may be implanted in the form of one or several pellets under the skin of the animal, or injected subcutaneously or intramuscularly in the form of a paste, solution or suspension.

Implants and injections can be designed to provide a daily drug release of generally from about 0.0005 mg to about 0.5 mg per kg of body weight, preferably from about 0.001 mg to about 0.2 mg per kg of body weight.

The present invention is further illustrated by the non-limiting examples set forth below.

EXAMPLE 1

Preparation of 1-Benzoyl-3-(1,2,3,4-tetrahydro-1-naphthyl)urea

A mixture of 1,2,3,4-tetrahydro-1-naphthylamine (10.01 g) and ether (100 ml) is stirred under a nitrogen atmosphere and a solution of benzoyl isocyanate (9.99 g) in ether (90 ml) is added dropwise. After the addition is completed, the mixture is stirred for 0.5 hour and cooled in ice. The product is collected and washed with cold ether (50 ml) to afford 15.7 g of the title compound, m.p. 166° to 169° C. Recrystallization from acetone affords 13.61 g, m.p. 171° to 173° C.

Similarly, substituted (X,Y)-benzoyl isocyanates are used in place of benzoyl isocyanate to afford the corresponding 1-(substituted-benzyol)-3-(1,2,3,4-tetrahydro-1- naphthyl)ureas, as follows:

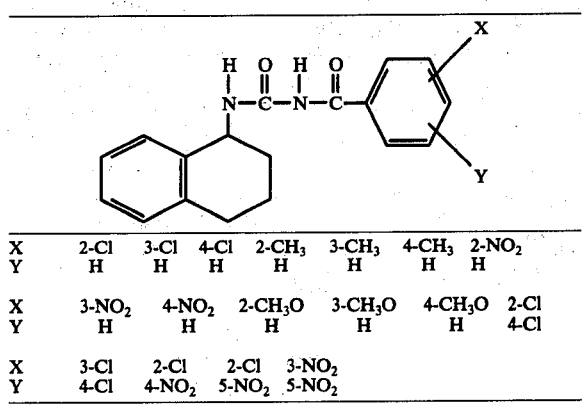

| X | 2-Cl | 3-Cl | 4-Cl | 2-CH$_3$ | 3-CH$_3$ | 4-CH$_3$ | 2-NO$_2$ |
| Y | H | H | H | H | H | H | H |
| X | 3-NO$_2$ | 4-NO$_2$ | 2-CH$_3$O | 3-CH$_3$O | 4-CH$_3$O | 2-Cl | |
| Y | H | H | H | H | H | 4-Cl | |
| X | 3-Cl | 2-Cl | 2-Cl | 3-NO$_2$ | | | |
| Y | 4-Cl | 4-NO$_2$ | 5-NO$_2$ | 5-NO$_2$ | | | |

The substituted-benzoyl isocyanates used above are readily prepared by reacting the corresponding substituted benzamides with oxalyl chloride in ethylene dichloride by the method of Speziale and Smith [J. Org. Chem., 28, 1805(1062))].

EXAMPLE 2

Preparation of 1,2,3,4-Tetrahydro-1-naphthylurea

A mixture of 1-benzoyl-3-(1,2,3,4-tetrahydro-1- naphthyl)urea (2.0 g) and aqueous sodium hydroxide (1N; 20 ml) is stirred and heated at reflux for 2.75 hours. The mixture is then cooled in ice and the product is collected and washed with water to afford 1.15 g of the title compound, m.p. 204° to 207° C.

Similarly, 1-(2-chlorobenzoyl)-, 1-(3-chlorobenzoyl)-, 1-(4-chlorobenzoyl)-, 1-(2-methylbenzoyl)-, 1-(3-methyl-benzoyl)-, 1-(4-methylbenzoyl)-, 1-(2-nitrobenzoyl)-, 1-(3-nitrobenzoyl)-, 1-(4-nitrobenzoyl)-, 1-(2 methoxybenzoyl)-, 1-(3methoxybenzoyl)-, 1-(4-methoxybenzoyl)-, 1-(2,4-dichloro-benzoyl)-,-dichlorobenzoyl)-, 1-(2-chloro-4-nitrobenzoyl)-, 1-(2-chloro-5-nitrobenzoyl)- and 1-(3,5-dinitrobenzoyl)- 3-(1,2,3,4-tetrahydro-1-naphthyl)urea are treated with aqueous sodium hydroxide to afford the title compound.

EXAMPLE 3

Preparation of N-(1,2,3,4-tetrahydro-4-oxo-1-naphthyl)formamides

A solution of 31.4 g of chromic anhydride is 140 ml of acetic anhydride is added dropwise over 80 minutes to a stirred solution of 20 g of N-formyl-1,2,3,4-tetrahydro-1-naphthylamine in 120 ml of acetic anhydride, while maintaining the temperature of the reaction mixture between −8° to 4° C. The reaction mixture is then stirred an additional 35 minutes at 3° C, into an ice-water mixture and stirred overnight. The mixture is filtered and 1.5 g of solid collected. The filtrate is saturated with sodium chloride and extracted with 2×1000 ml of methylene chloride. The combined organic extracts are washed with 1000 ml of brine and evaporated to dryness in vacuo. The oily residue is triturated with 200 ml of ether to afford a tan solid, the mixture stirred for a while and is then filtered. The collected tan solid is washed with 2×5 ml of ether to afford 13 g of product, melting point 103° to 106° C.

Substitution of sodium or potassium bichromate in the above reaction also affords the title compound.

The title compound is a also prepared by reacting N-(1,2,3,4-tetrahydro-1-naphthyl)formamide with four equivalents of ceric sulfate or ceric ammonium nitrate in 50% aqueous acid at room temperature for 10 minutes. The reaction mixture is then filtered, poured into water and extracted with chloroform. The chloroform extract is evaporated to dryness in vacuo to afford the title compound.

Similarly, (+)- and (−)-N-(1,2,3,4-tetrahydro-1-naphthyl)formamides are oxidized by the above procedures to afford (+)- and (−)-N-(1,2,3,4-tetrahydro-4-oxo-1-naphthyl)- formamides.

EXAMPLE 4

Preparation of 1,2,3,4-Tetrahydro-4-oxo-1-naphthylamine hydrochloride

A solution of 19.6 g of N-formyl-1,2,3,4-tetrahydro-4-oxo-1-naphthylamine in 214 ml of 95% ethanol and 214 ml of 2N hydrochloride acid is heated at reflux for 3 hours and then stirred at room temperature for 2 days. The solution is filtered and the filtrate concentrated in vacuo to afford a dark residue. The residue is dried using ethanol to remove water in vacuo and this procedure affords 20.2 g of the title compound, m.p. 200° to 216° C (dec.).

The amine hydrochloride is mixed with aqueous sodium hydroxide solution (10%), the mixture is stirred at room temperature for 6 hours and is then extracted with chloroform. The chloroform extract is evaporated to dryness in vacuo to afford 1,2,3,4-tetrahydro-4-oxo-1-napthylamine.

EXAMPLE 5

Preparation of 1-Benzoyl-3-(1,2,3,4-tetrahydro-4-oxo-1-naphthyl)urea

A solution of 1,2,3,4-tetrahydro-4-oxo-1-naphthylamine (5.23 g) in dry methylene chloride (75 ml) is stirred under a nitrogen atmosphere and a solution of benzoyl isocyanate (4.77 g) in ether (35 ml) is added dropwise. After the addition is completed, the mixture is stirred for 1 hour and then cooled in ice. The product is collected and washed.

Similarly, benzoyl isocyanate is replaced by substituted (X,Y)-benzoyl isocyanates to afford the following 1-(substituted-benzoyl)-3-(1,2,3,4-tetrahydro-4-oxo-1-naphthyl)ureas:

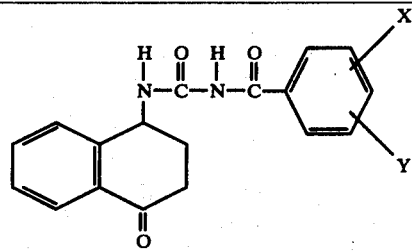

| X | 2-Cl | 3-Cl | 4-Cl | 2-NO₂ | 3-NO₂ | 4-NO₂ | 2-CH₃ |
| Y | H | H | H | H | H | H | H |
| X | 3-CH₃ | 4-CH₃ | 2-CH₃O | 3-CH₃O | 4-CH₃O | 2-Cl | |
| Y | H | H | H | H | H | 3-Cl | |
| X | 3-Cl | 2-Cl | 2-Cl | 3-NO₂ | | | |
| Y | 4-Cl | 4-NO₂ | 5-NO₂ | 5-NO₂ | | | |

EXAMPLE 6

Preparation of 1,2,3,4-Tetrahydro-4-oxo-1-naphthylurea

A mixture of 1-benzoyl-3-(1,2,3,4-tetrahydro-4-oxo-1-naphthyl)urea (3.8 g) and aqueous sodium hydroxide (2N; 38 ml) is stirred and heated at reflux for 70 minutes. The mixture is then cooled in ice and the product is collected and washed with water to afford 1.83 g of the title compound, m.p. 212° to 215° C.

Similarly, replacing 1-benzoyl-3-(1,2,3,4-tetrahydro-4-oxo-1-naphthyl)urea with 1-(2-chlorobenzoyl)-, 1-(3-chlorobenzoyl)-, 1-(4-chlorobenzoyl)-, 1-(2-nitrobenzoyl)-, 1-(3- nitrobenzoyl)-, 1-(4-nitrobenzoyl)-, 1-(2-methylbenzoyl)-, 1-(3-methylbenzoyl)-, 1-(4-methylbenzoyl)-, 1-(2-methoxy benzoyl)-, 1-(3-methoxybenzoyl)-, 1-(4-methoxybenzoyl)-, 1-(2,4-dichlorobenzoyl)-, 1-(3,4-dichlorobenzoyl)-, 1-(2- chloro-4-nitrobenzoyl)-, 1-(2-chloro-5-nitrobenzoyl)- and 1-(3,5-dinitrobenzoyl)-3-(1,2,3,4-tetrahydro-4-oxo-1naphthyl)urea, respectively, affords the title compound.

EXAMPLE 7

Mouse Growth Regulant Tests

CFI female mice from Carworth Farm are received when they are 6 weeks old. They are housed 10 to a cage in air-conditioned room (72°-76° F) with automatically controlled lights, 14 hours, on and 10 hours off. The basal diet used in these studies is Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Tables.

Twelve days later the mice are weighted again and the experiment terminated. At least three cages (30 mice) of untreated controls are included in each test. Test data are provided in Table I below; wherein data are reported as percent weight gain over controls. The following is a description of a diet to which the growth-promoting compounds are added.

| DIET GUARANTEED ANALYSIS | |
|---|---|
| Crude protein not less than | 23.0% |
| Crude fat not less than | 4.5% |
| Crude fiber not more than | 6.0% |
| Ash not more than | 9.0% |
| INGREDIENTS | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewer's dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

Table I

Effectiveness of 1,2,3,4-Tetrahydro-4-oxo-1-naphthylurea as Animal Growth-Promoting Agent Reported as Percent Weight Gain Over Controls Using Mice as the Test Animal

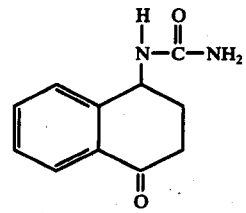

| Rate ppm in Diet | % Weight Gain Over Controls |
|---|---|
| 50 | 35.71 |
| 100 | 97.40 |
| 200 | 93.51 |
| 50 (levorotatory) | 53.2 |

EXAMPLE 8

Preparation of (−)-1,2,3,4-Tetrahydro-4-oxo-1-naphthylurea

In the manner described in Example 5, (+)-1,2,3,4-tetrahydro-4-oxo-1-naphthylamine, which is obtaind by acid hydrolysis (refluxing in HCl)of (−)-N-(1,2,3,4-tetrahydro-4- oxo-1-naphthyl)formamide followed by neutralization, is allowed to react with benzoyl isocyanate. The resulting 1-benzoyl-3-(1,2,3,4-tetrahydro-4-oxo-1-naphthyl)urea is then hydrolyzed with alkali as in Example 6 to afford (−)-1,2,3,4-tetrahydro-4-oxo-1-naphthylurea.

(−)-N-(1,2,3,4-tetrahydro-4-oxo-1-naphthyl)formamide is obtained by the method of Example 3 by starting with the (−)-N-(1,2,3,4-tetrahydro-1-naphthyl)formamide, which is obtained by azeotroping the parent (+)-amine with 98% HCOOH/toluene.

EXAMPLE 9

Preparation of 1-Benzoyl-3-(1,2,3,4-tetrahydro-4-oxo-1-naphthyl)urea

A sample of 1-benzoyl-3-(1,2,3,4-tetrahydro-1-naphthyl)urea is oxidized with ceric ammonium nitrate in the manner described in Example 3 to afford 1-benzoyl-3-(1,2,3,4- tetrahydro-4-oxo-1-naphthyl)urea.

We claim:

1. A compound of the formula:

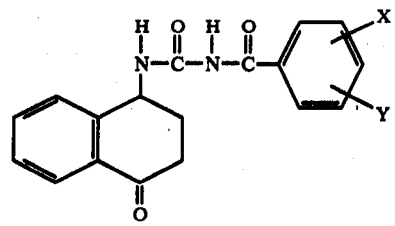

wherein X is selected from the group consisting of hydrogen, methyl, methoxy, chloro and nitro; Y is selected from the group consisting of hydrogen, chloro and nitro; and the racemic mixture and the optical isomers thereof.

2. The compound according to claim 1, racemic 1-benzoyl-3-(1,2,3,4-tetrahydro-4-oxo-1-naphthyl)urea.

3. The optically active compound according to claim 1, (1S)-benzoyl-3-(1,2,3,4-tetrahydro-4-oxo-1-naphthyl) urea.

4. The optically active compound according to claim 1, (1R)-benzoyl-3-(1,2,3,4-tetrahydro-4-oxo-1-naphthyl) urea.

5. A process for the preparation of a compound, racemic mixture and optical isomers thereof, of the formula:

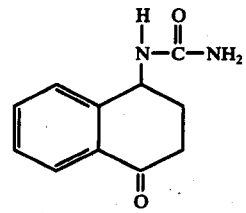

which comprises hydrolyzing a compound of the formula:

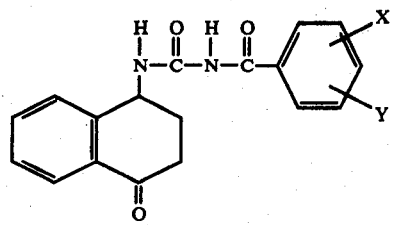

wherein X is selected from the group consisting of hydrogen, methyl, methoxy, chloro and nitro; Y is selected from the group of consisting of hydrogen, chloro and nitro; and the racemic mixture and the optical isomers thereof.

6. A process according to claim 5, wherein X and Y are both hydrogen; and the racemic mixture and the optical isomers thereof.

* * * * *